United States Patent
Solar

[19]

[11] Patent Number: 5,549,635
[45] Date of Patent: *Aug. 27, 1996

[54] NON-DEFORMABLE SELF-EXPANDING PARALLEL FLOW ENDOVASCULAR STENT AND DEPLOYMENT APPARATUS THEREFORE

[75] Inventor: Ronald J. Solar, San Diego, Calif.

[73] Assignee: Solar, Rita & Gaterud, Ltd., San Diego, Calif.

[*] Notice: The term of this patent shall not extend beyond the expiration date of Pat. No. 5,403,341.

[21] Appl. No.: 415,846

[22] Filed: Apr. 3, 1995

Related U.S. Application Data

[63] Continuation-in-part of Ser. No. 185,549, Jan. 24, 1994, Pat. No. 5,403,341.

[51] Int. Cl.$^6$ .................................................. A61M 29/00
[52] U.S. Cl. .................................. 606/198; 623/1; 623/12
[58] Field of Search ................................... 623/1, 11, 12; 606/108, 191, 194, 195, 198; 604/96

[56] References Cited

U.S. PATENT DOCUMENTS

| | | |
|---|---|---|
| 4,580,568 | 4/1986 | Gianturco . |
| 4,733,665 | 3/1988 | Palmaz . |
| 4,830,003 | 5/1989 | Wolff et al. . |
| 4,922,905 | 5/1990 | Strecker . |
| 4,950,227 | 8/1990 | Savin et al. . |
| 5,035,706 | 7/1991 | Giantureo et al. . |
| 5,041,126 | 8/1991 | Gianturco . |
| 5,108,416 | 4/1992 | Ryan et al. . |
| 5,135,536 | 8/1992 | Hillstead . |
| 5,161,547 | 11/1992 | Tower . |
| 5,282,824 | 2/1994 | Gianturco . |
| 5,292,331 | 3/1994 | Boneau ........................................ 623/1 |
| 5,403,341 | 4/1995 | Solar ........................................... 623/1 |

OTHER PUBLICATIONS

Abstract for Raychem Corp.EP 183372A Publication Date Oct. 1995.
Abstract for Cordis Corp. EP 378161A Publication Date Jul. 1990.
Abstract for Zeta Ltd. EP 246998A Publication Date May 1987.

*Primary Examiner*—Michael H. Thaler
*Assistant Examiner*—William Lewis
*Attorney, Agent, or Firm*—Stentina Brunda & Buyan

[57] ABSTRACT

A non-deformable, self-expanding stent device, and deployment catheter therefore. The stent device comprises an elongate wire member having a multiplicity of back and forth bends formed therein to define a series of side-by-side straight segments, the ends of said wire being coupled to one another such that said straight segments are disposed in a cylindrical array about a longitudinal axis. The stent is initially disposed in an operative configuration whereby the stent has a first internal diameter, and wherein the straight segments are generally parallel to one another. The stent is foldable or compressible to a contract configuration wherein the stent has an outer diameter or outer cross sectional dimension which is smaller than the first inner diameter of the operatively configured stent. The stent is formed of resilient material such that the stent is biased to, and will automatically self-expand to, its operative configuration. The preferred deployment catheter comprises an elongate catheter body having a balloon mounted thereon. The stent is positioned on the deflated balloon and folded or compacted to its compact configuration. One or more breakable retainer sheaths are positioned about the stent to hold the stent in its compact configuration on the balloon. The stent-bearing balloon catheter is advanceable into an anatomical passageway. Thereafter, the balloon is inflated to cause the breakable sheaths to tear, thereby releasing the stent and allowing the stent to undergo in situ self-expansion to its operative configuration within the anatomical passageway.

30 Claims, 3 Drawing Sheets

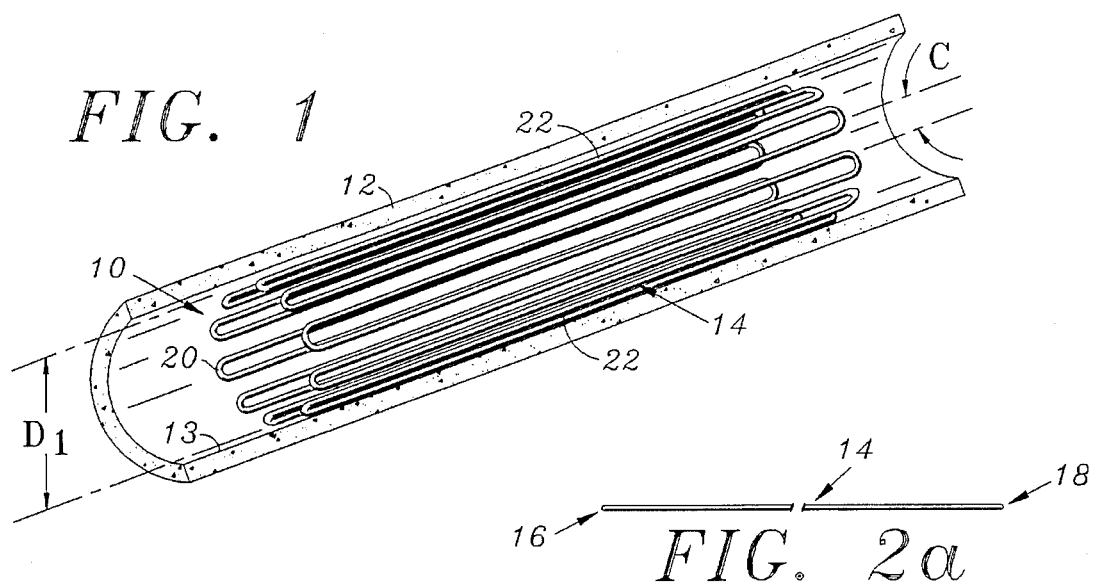
FIG. 1
FIG. 2a
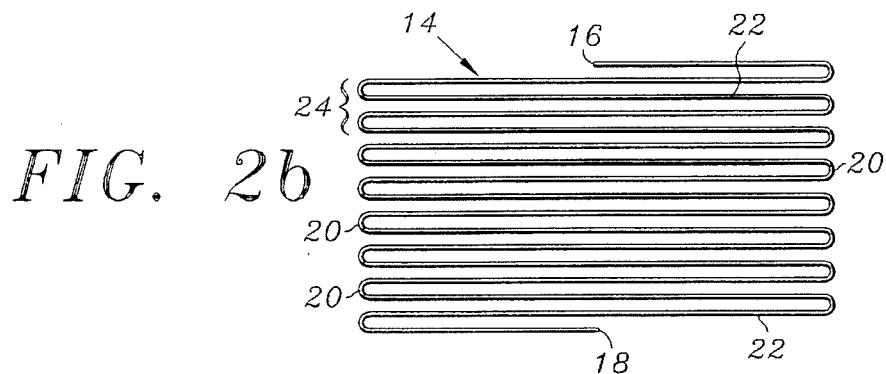
FIG. 2b
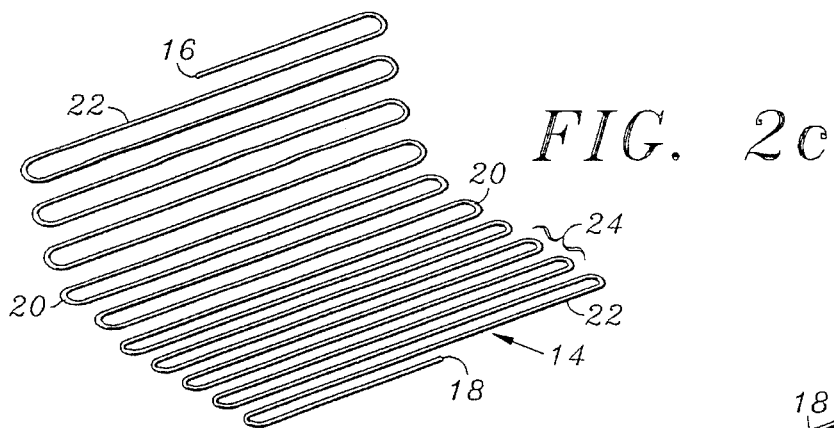
FIG. 2c
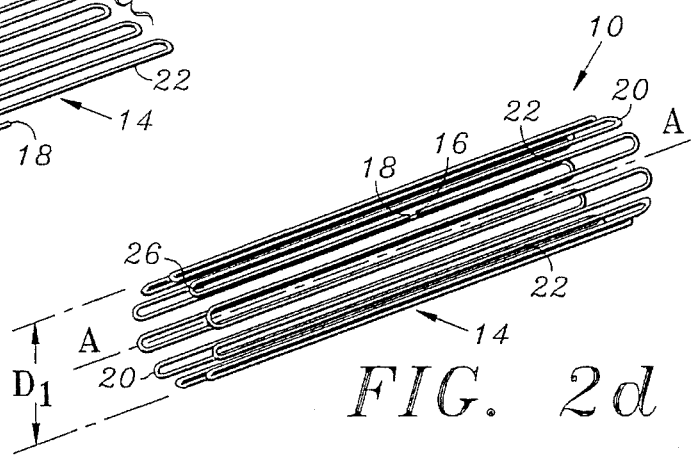
FIG. 2d

NON-DEFORMABLE SELF-EXPANDING PARALLEL FLOW ENDOVASCULAR STENT AND DEPLOYMENT APPARATUS THEREFORE

RELATED APPLICATION

This application is a continuation-in-part of Ser. No. 08/185,549 entitled PARALLEL FLOW ENDOVASCULAR STENT AND DEPLOYMENT APPARATUS THEREFORE which was filed on Jan. 24, 1994, and which will issue on Apr. 4, 1995 as U.S. Pat. No. 5,403,341.

FIELD OF THE INVENTION

The present invention pertains generally to medical equipment, and more particularly to endoprosthetic stent devices and apparatus for deploying the same.

BACKGROUND OF THE INVENTION

Endoprosthetic devices commonly referred to as a "stents" generally comprise a rigid structural member which may be implanted within an anatomical structure to reinforce or support a portion of the anatomical structure which has become occluded, weakened, compressed or otherwise affected by pathology. Stent devices of various configuration have heretofore been successfully utilized to reinforce or dilate numerous types of anatomical structures, including blood vessels, urogenital passageways and bile ducts.

In cardiovascular applications, endovascular stents are typically inserted into a blood vessel to dilate areas of the vessel which have become occluded by atherosclerotic plaque or constricted by an adjacent tumor. Insertion and endovascular deployment of the stent may be accomplished either intraoperatively through an open incision or percutaneously through a transluminally positioned catheter or similar introducer apparatus.

Endovascular stents of the prior art have typically fallen into two general categories of construction. The first category of endovascular stent is the self-expanding stent formed of spring metal or similar material and deployable through the lumen of a tubular catheter or sleeve such that, when the self-expanding stent is advanced out of the distal end of the catheter or sleeve, it will automatically expand so as to exert pressure against the surrounding blood vessel wall. The second category of stent is the pressure-expandable stent. Pressure-expandable stents are typically formed of rigid, pre-set material and may be deployed on an inflatable balloon or other expanding member such that, upon inflation of the balloon or expansion of the deployer, the stent will be radially enlarged to a desired diameter such that the stent becomes positioned against the surrounding blood vessel wall.

Self-expanding endovascular stents of the prior art include those described in U.S. Pat. Nos. 4,580,568 (GIANTURCO); and 4,830,003, (WOLFF, et al.) and foreign patent publication no. EP 183372A.

Pressure-expandable endovascular stents of the prior art include those described in U.S. Pat. Nos. 5,135,336 (HULSTEAD); 4,733,685 (PALMATZ); 4,922,905 (STRECKER); 4,950,227 (SAVIN, et al.); 5,041,126 (GIANTURCO); 5,108,416 (RYAN, et al.) 5,161,547 (TOWER) (and foreign patent publications nos. EP-378151A; and EP46998A.

In clinical practice, the utilization of endovascular stent devices has generally been associated with an incidence of thromboembolic complications. Such thromboembolic complications are believed to result, at least in part, due to a) disruption of laminar blood flow by the stent itself and/or b) non-biocompatibility of the stent material.

In view of the clinical incidence of thromboembolic complications experienced with endovascular stent devices of the prior art, there remains a need for newly designed endovascular stent devices which promote non-turbulent laminar blood flow through the lumen of the blood vessel and which minimize the surface area of stent-host interface so as to minimize potential complications due to non-biocompatibility of the stent.

SUMMARY OF THE INVENTION

In accordance with the invention, there is provided a non-formable, self-expanding stent device, comprising an elongate wire member having first and second ends, said elongate wire member having formed therein a series of radius bends, at spaced-apart locations, the angle of each such radius bend being approximately 180° so as to form a series of multiple straight segments of the wire member disposed in generally parallel, convoluted relation to one another. The first and second ends of the wire member are drawn into coaxial alignment and fused or coupled to one another so to configure the stent in an "operative" configuration wherein the straight segments of the wire disposed in a cylindrical array about a longitudinal axis, and wherein there is defined an internal flow channel of a first internal diameter ($D_1$). The stent is formed of material, such as titanium wire, which is sufficiently resilient to permit the stent to be compacted or folded to a "compact" configuration wherein the stent has an outer diameter or cross-sectional dimension ($D_2$) which is smaller than its original internal flow channel diameter ($D_2$). The stent may be held or maintained in such compact configuration to permit delivery of the stent into an anatomical passageway or structure. Thereafter, the means by which the stent is held in such compact configuration is removed or negated, thereby permitting the stent to resiliently self-expand to its operative configuration ($D_1$). When so expanded to its operative configuration within an anatomical passageway, the straight segments of the stent are disposed in generally parallel relation to one another and are generally parallel to the axis of flow through the anatomical passageway, thereby minimizing the turbulence or flow disruption created by the presence of the stent within the anatomical passageway.

The non-deformable, self-expanding stent device of the present invention may be inserted an implanted in an anatomical structure or passageway by any suitable deployment apparatus usable therefore, including the various encapsulation devices, retractable sleeves and tubular catheters heretofore known to be usable or delivery of self-expanding stents. Alternatively, the self-expanding stent device of the present invention may be deployed or delivered into an anatomical structure or passageway by using the particular stent deployment catheter of the present invention, as described herebelow.

The stent deployment catheter of the present invention comprises a) a balloon, typically disposed on a catheter (i.e., a balloon catheter) and b) one or more tearable retaining sheaths. The stent device is initially positioned over the balloon and is compressed or folded to its "compact" configuration thereon. At least one tearable sheath is then disposed about at least a portion of the stent to hold the stent on the balloon in its compact configuration. Thereafter, when it is desirable to release the stent, the balloon is inflated to exert outward pressure on the tearable sheath(s). Such pressure exerted by the balloon causes the sheath(s) to tear, thus resulting in release of the stent device. The stent device, when so released, is permitted to self-expand to its "operative" configuration. The stent may be size matched to the anatomical passageway such that, when the stent expands to its operative configuration it will radially engage the surrounding wall of the anatomical passageway. Thereafter, the balloon may be deflated and the deployment catheter (including the torn sheaths) may be retracted and removed from the anatomical passageway, thereby allowing the self-expanded stent to remain operatively positioned within the anatomical passageway.

The stent device and/or stent delivery apparatus of the present invention may be utilized during open surgical procedures by passing the deployment apparatus, having the stent positioned thereupon, through an incision which provides access into the anatomical passageway wherein the stent is to be positioned. Alternately, the stent and/or stent deployment apparatus may be inserted percutaneously, and subsequently advanced transluminally into the desired anatomical passageway. In applications wherein the anatomical passageway comprises a blood vessel, the stent device may be utilized for the purpose of restoring or maintaining patency of a previously occluded area of atherosclerotic disease. In this regard, the devices of the present invention may be utilized subsequent to or in conjunction with a balloon dilation angioplasty procedure.

Also, the stent devices and/or stent delivery apparatus of the present invention may be used as a support structure or anchoring apparatus for various tubular endovascular grafts of the type usable to repair aneurysms and/or to otherwise recanalize a blood vessel without open surgical exposure of the blood vessel.

Further aspects, objects and advantages of the present invention to those skilled in the art upon reading and understanding of the following detailed description, and upon consideration of the accompanying drawings.

BRIEF DESCRIPTION OF THE DRAWINGS

These, as well as other features of the present invention, will become more apparent upon reference to the drawings wherein:

FIG. 1 is a perspective view of the stent device of the present invention as operatively positioned within an anatomical passageway;

FIG. 2a is a side view of the wire member from which the stent is formed;

FIG. 2b is a side elevational view illustrating the manner in which the wire member is bent at spaced locations along the length thereof during the process of fabricating the stent device;

FIG. 2c is a perspective view illustrating the manner in which the opposed ends of the wire member are drawn toward each other subsequent to the bending of the wire member in the manner shown in FIG. 2b;

FIG. 2d is a perspective view of the stent device as formed by the attachment of the opposed ends of the wire member to each other;

DETAILED DESCRIPTION OF THE PREFERRED EMBODIMENTS

Figure 3A:
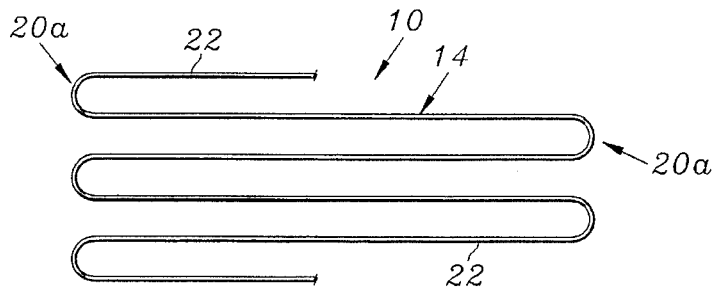
FIG. 3a is a partial side elevational view of an alternative embodiment of the stent of the present invention.

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments that are also intended to be encompassed within the spirit and scope of the invention.

THE PREFERRED STENT DEVICE AND DEPLOYMENT CATHETER

Referring now to FIG. 1, perspectively illustrated is a stent device 10 constructed in accordance with the preferred embodiment of the present invention as operatively positioned within an anatomical passageway 12 such as a blood vessel. As will be discussed in more detail below, the stent 10 may be utilized to reinforce or dilate numerous types of anatomical passageways, including blood vessels, urogenital passageways and bioducts. In relation to cardiovascular applications, the stent 10 is typically inserted into a blood vessel to dilate areas of the vessel which have become occluded by atherosclerotic plaque or constricted by an adjacent tumor.

Referring now to FIGS. 2a–2d, the stent 10 is formed from an elongate wire member 14 defining a first end 16 and a second end 18. The wire member 14 is preferably fabricated from a titanium alloy, though other biocompatible materials of similar resiliency may be utilized as an alternative. The wire member 14 is manipulated in a manner defining a multiplicity of radius bends 20 which are formed at spaced locations along the length thereof. Each of the bends 20 preferably forms an angle of approximately 180° so as to define multiple straight segments 22 of the wire member 14 between the bends 20. As best seen in FIG. 2b, the straight segments 22 defined between the radius bends 20 are disposed in generally parallel, convoluted relation to one another. Due to the formation of the radius bends 20 and straight segments 22, the wire member 14 defines a multiplicity of convolutions 24, each of which are formed by an adjacent pair of straight segments 22 and a single radius bend 20. The wire member 14 shown in FIG. 2b includes eight (8) convolutions formed therein, while the wire member 14 shown in FIG. 2c includes ten (10) convolutions formed therein. In the preferred embodiment, the radius bends 20 are formed in the wire member 14 via the engagement of the wire member 14 to a suitable mandrel, though it will be recognized that other formation techniques may also be utilized.

When the wire member 14 is bent to define the desired number of convolutions 24, the first end 16 of the wire member 14 terminates at approximately the mid-point of the adjacent straight segment 22. Similarly, the second end 18 of the wire member 14 terminates at approximately the midpoint of the straight segment 22 adjacent thereto. The wire member 14 possesses sufficient flexibility so as to allow the first end 16 to be rolled toward the second end 18 in the manner shown in FIG. 2c subsequent to the formation of the convolutions 24 therewithin. As seen in FIG. 2d, the convoluted wire member 14 is rolled so as to position the first end 16 thereof into coaxial alignment with the second end 18. Thereafter, the first end 16 is fused to the second end 18. Such fusion is preferably facilitated via a welding process, though other attachment methods may be utilized. When the first and second ends 16, 18 are properly attached to each other, the straight segments 22 of the wire member 14 assume a generally cylindrical array about a longitudinal axis A and define therewithin an internal flow channel 26 having a first internal diameter $D_1$.

In the preferred embodiment, the stent 10 is compressed or folded from its "operative" configuration having inner diameter $D_1$ to its "compact" configuration having an outer diameter (or other cross-sectional dimension) $D_2$, prior to being delivered to its intended placement site within the anatomical passageway 12. When in its desired placement location, the stent device 10 is allowed to self-expand from its "compact" configuration to its "operative" configuration, thereby causing the stent 10 to radially engage the inner wall 13 of the anatomical passageway 12. Such placement of the stent 10 serves to maintain the patency of the anatomical passageway 12 or to otherwise hold the stent (along with any accompanying apparatus such as an endovascular graft) in fixed position within the passageway 12. The manner in which the stent 10 is delivered and released at its intended implantation site is discussed in more detail below.

Figure 5A:
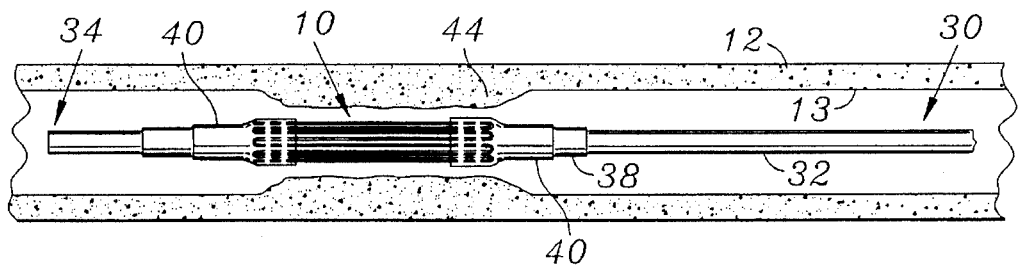
FIG. 5a shows a first stage of a preferred method for delivering a stent of the present invention using the stent delivery apparatus of the present invention.
Figure 5B:
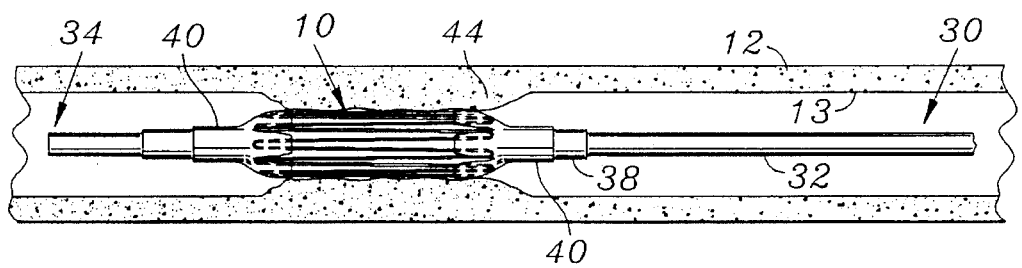
FIG. 5b shows a second stage of a preferred method for delivering a stent of the present invention using the stent delivery apparatus of the present invention.
Figure 5C:
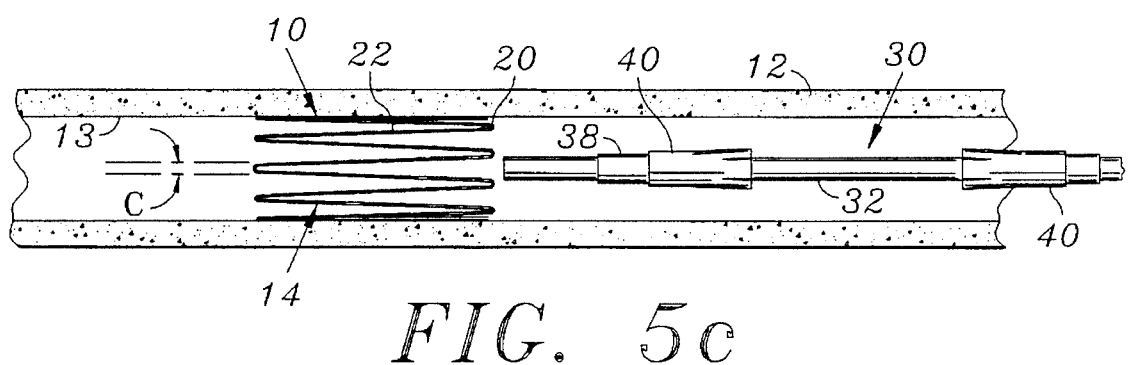
FIG. 5c shows a third stage of a preferred method for delivering a stent of the present invention using the stent delivery apparatus of the present invention.

As seen in FIGS. 1 and 5c, the operatively configured stent 10 is sized such that when the flow channel 26 is expanded to its full internal diameter $D_1$ the straight segments 22 are substantially parallel (i.e., preferably no more than 5° out of parallel) to one another. As will be recognized, the relationship of the straight segments 22 to the longitudinal axis A of flow through the passageway 12 is determinative of the amount of flow disruption or turbulence which will result from placement of the stent 10 within the passageway 12. Thus, the substantially parallel disposition of the straight segments 22 relative to the axis of flow A results in a minimization of turbulence-induced thromboembolic complications when the stent is placed within a blood vessel.

The size of the stent 10 is a function of the number of convolutions 24 formed therein and total length of the wire member 14. The number of convolutions 24 formed within the stent 10 is selected based on the internal diameter of the anatomical passageway 12 into which the stent 10 is to be operatively positioned.

Figure 3B:
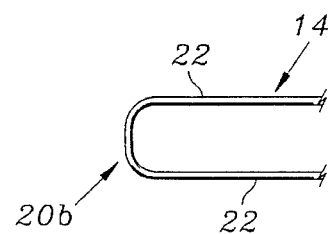
FIG. 3b is a partial side elevational view show an alternative bend configuration useable in forming the stents of the present invention.

The number of convolutions 24, and the radius and/or configuration of the radius bends 20 may be varied, depending on the intended size and function of the stent 10. For example, in the embodiment shown in FIGS. 1–2 and 4–5, the stent comprises a relatively large number of straight segments 22, having relatively small radius bends 20 formed therebetween. Alternatively, the embodiment shown in FIG. 3a utilizes fewer straight segments 22 and incorporates larger radius bends 20a, as shown. Additionally, it will be appreciated that the linear or squared bends 20b, as shown in FIG. 3b, may be utilized in place of the generally rounded radius bends 20, 20a shown in the preferred embodiment.

Figure 4B:
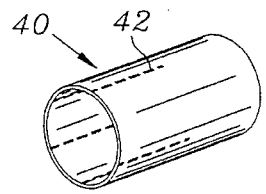
FIG. 4b is an enlarged perspective view of a retaining sheath utilized to maintain the stent device in position upon the balloon of the balloon catheter.
Figure 4A:
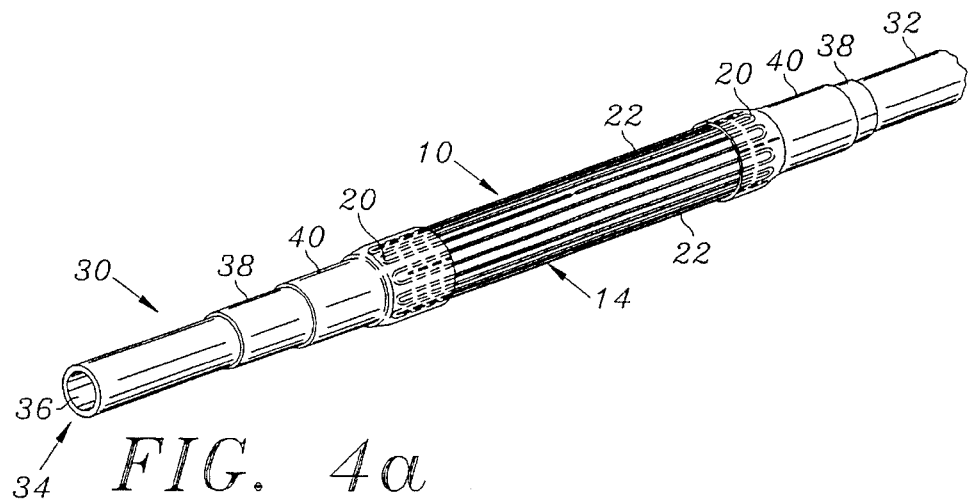
FIG. 4a is an enlarged perspective view of the distal portion of a balloon catheter having the stent device operatively positioned thereupon.

Referring to FIG. 4a, self-expanding the stent 10 is preferably utilized in conjunction with a deployment catheter 30 which facilitates insertion, positioning, release and in situ self-expansion of the stent 10, within an anatomical passageway such as a blood vessel. The deployment catheter 30 generally comprises an elongate catheter body 32 defining an open distal end 34 and a hollow lumen 36 extending longitudinally therethrough. Positioned upon the outer surface of the catheter body 32 adjacent the distal end 34 thereof is an inflatable balloon 38 and a set of tearable retaining sheaths 40. The balloon 38 may comprise a cylindrical elastic member, the opposed ends of which are attached to the outer surface of the catheter body 32, typically via a heat sealing process. The balloon is inflatable to a diameter which causes the retaining sheaths 40 to tear, thereby releasing the stent 10, and permitting the stent to self-expand in situ. Although not shown, the catheter body 32 includes a balloon inflation lumen which is in fluid communication with the inflation space defined between the balloon 38 and the outer surface of the catheter body 32 for selectively inflating and deflating the balloon 38. However, it will be recognized that the catheter body 32 may be formed with a closed distal end 34, and that the lumen 36 may function as the balloon inflation lumen.

In an alternative construction, the inflatable balloon 38 may comprise an integral portion of the catheter body sized and located so as to effect the intended tearing of the retaining sheaths 32, when inflated.

In the preferred embodiment, the stent 10 is extended over the catheter body 32 such that the deflated balloon 38 is centrally disposed within the flow channel 26. The stent 10 is compresses or folded to its compact configuration ($D_2$) and the retaining sheaths 40 are mounted around the ends of the compact stent 10 to hold the stent 10, in its compact configuration, on the outer surface of the deflated balloon 38, as shown in FIG. 4a.

As best seen in FIG. 4b, each of the retaining sheaths 40 has a generally cylindrical configuration and is provided with sets of perforations 42 which extend longitudinally from one end of the sheath 40 to the approximate mid-point thereof. As seen in FIG. 4a, the retaining sheaths 40 are interfaced to the stent 10 and dilation balloon 38 such that the portions thereof including the perforations 42 disposed therein are extended over (i.e., overlap) the ends of the stent 10, with the non-perforated portions being directly engaged to the outer surface of the balloon 38. The retaining sheaths 40 are preferably formed of plastic which is weakened or perforated such that the retaining sheaths 40 will tear away from the ends of the stent 10 as the balloon 38 is inflated.

The retaining sheaths 40 may be formed of any suitable material. In some embodiments, the retaining sheaths 40 may be formed of heat shrinkable plastic material and such retaining sheaths 40 may be heat shrunk into place on the ends of the stent 10. In alternative embodiments, the retaining sheaths 40 may be formed of soft pliable elastomeric material such as silicone polyurethane or latex, although such materials may not be heat shrinkable. In such embodiments, the elastomeric materials may be elastically expanded and allowed to elastically contract into place on the ends of the stent 10 or, alternatively, may be initially swelled by solvent application and subsequently allowed to post-contract about the outer surface of the catheter body and over the ends of the stent 10, as shown.

Figure 4C:
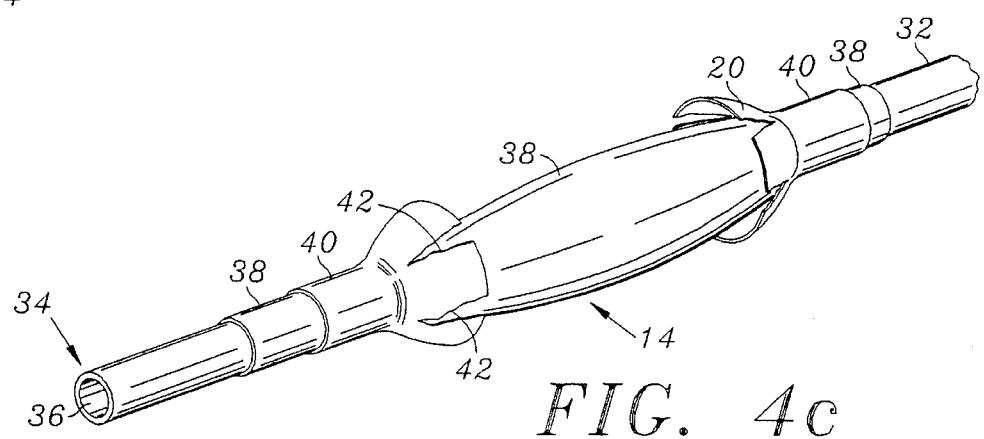
FIG. 4c is an enlarged perspective view of the distal portion of a balloon catheter wherein the balloon is inflated to tear the retaining sheaths.

As seen in FIG. 4c, when the balloon 38 having the stent 10 positioned thereabout is inflated, the retaining sheaths 40 are adapted to tear under pressure as the balloon 38 is inflated. Such tearing of the sheaths 40 release the stent 10, thus allowing the stent to self-expand from its compact configuration ($D_2$) to its operation configuration ($D_1$).

The locations of the perforations 42 within the retaining sheaths 40, causes only those portions of the sheaths 40 which are extended over the opposed ends of the stent 10 to be torn by the expansion of the balloon 38, thus preventing the remaining portions of the sheaths 40 from becoming torn away from attachment to the balloon 38 and or catheter body 32. Such residual attachment of the torn sheaths 40 ensures that the torn sheaths 40 may subsequently be extracted and removed along with the deployment catheter 30. Importantly, when the stent 10 has fully self expanded into engagement with the inner wall 13, the torn ends of the retaining sheaths 40 are not captured between the expanded stent 10 and the inner wall 13. As such, subsequent to the deflation of the balloon 38, the catheter body 32, balloon 38 and torn retaining sheaths 40 (shown in FIG. 4c) may easily be pulled proximally through and out of the internal flow channel 26 of the stent 10, thus leaving the stent 10 operatively positioned at the treatment site within the anatomical passageway 12.

It will be appreciated that the balloon 38 need only inflate to a diameter which is sufficient to cause tearing or breaking of the retaining sheaths 40. In this regard, the maximal inflation limit of the balloon may be such that the outer diameter of the balloon tears the retaining sheaths 40 but does not fully occlude or fully block the lumen of the anatomical passageway (e.g., blood vessel) within which the stent 10 is being placed. The self-expandability of the stent will cause the stent to expand to its full operative configuration ($D_1$) despite the fact that the maximal diameter of the inflated balloon 38 may be substantially less than the internal diameter $D_1$ of the operatively configured stent.

METHOD FOR DEPLOYMENT AND IMPLANTATION OF THE STENT

Referring now to FIGS. 5a–5c, the stent 10 of the present invention is utilized by initially positioning the stent 10 upon the balloon 38 of the deployment catheter 30 and thereafter compressing and folding the stent to its compact configuration. The ends of the stent 10 are then wrapped by the retaining sheaths 40 in the aforementioned manner to hold the stent 10 in its compact configuration upon the balloon 38. Thereafter, the deployment catheter 30, having the compacted stent 10 positioned thereon, is inserted and transluminally advanced through the anatomical passageway 12 to its desired placement site, such as the location of an existing or previously balloon-dilated atherosclerotic plaque occlusion 44. After the balloon 38 and stent 10 have been positioned at the desired placement site, the balloon 38 is inflated via the inflation lumen, thus causing the perforations 42 of the sheaths 40 to tear (FIG. 5b), and thus releasing the stent 10. The stent then self-expands to its operative configuration ($D_1$). Such expansion of the stent 10 causes the stent 10 to radially engage the inner wall 13 of the anatomical passageway 12 and to exert sufficient radial outward pressure thereon to perform the required function of the stent (e.g., to maintain patency of the passageway 12). The balloon 38 is then deflated, and the deployment catheter 30 is removed (FIG. 5c) from the anatomical passageway 12, thus allowing the stent 10 to remain operatively positioned at the desired placement site therewithin.

The preferred method of the present invention may be carried out percutaneously, or by way an open surgical procedure. When used during an open surgical procedure the deployment catheter 30 having the stent 10 positioned thereupon is initially passed through an incision which provides access into the anatomical passageway 12. Alternatively, when inserted percutaneously, the deployment catheter 30 having the stent 10 positioned thereupon is passed percutaneously through a tubular introducer and subsequently transluminally advanced into the anatomical passageway 12 to the occlusion 44 therewithin. When the anatomical passageway 12 in which the stent 10 is utilized comprises a blood vessel, the treatment site typically is an area of atherosclerotic plaque occlusion or a compressed area of the blood vessel which has been affected by a tumor or other pathology. Additionally, the present method is typically carried out subsequent to a balloon dilation angioplasty, or any other type of angioplasty procedure at the treatment site.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

What is claimed is:

1. A stent delivery system, said system comprising:

a self expanding stent device comprising:

i) an elongate wire member having first and second ends, a multiplicity of back and forth bends being formed in said wire member at spaced-apart locations, so as to form said wire member into a series of side-by-side straight segments, the first and second ends of said wire member being coupled to one another such that said straight segments are disposed in a cylindrical array around a longitudinal axis;

ii) said stent device being alternately configureable in an operative configuration wherein said straight segments are substantially parallel to one another and disposed in said cylindrical array about said longitudinal axis so as to define a central passageway extending longitudinally therethrough and having a first diameter; and, iii) a compact configuration wherein said straight segments are compacted such that said stent has an outer cross sectional dimension which is smaller than said first diameter;

iv) said wire member being formed on resilient material and biased to said operative configuration such that, when unrestrained, said stent device will automatically expand from its said compact configuration to its said operative configuration;

a deployment catheter for delivering said stent device into an anatomical passageway, said deployment catheter comprising: and, i) an elongate catheter body;

ii) an inflatable balloon positioned on said catheter body;

iii) an inflation lumen extending through said catheter body for passing inflation fluid into and out of said balloon; and, said stent device being positioned on said elongate catheter body with said inflatable balloon in its deflated state, such that said inflatable balloon in disposed within said stent device; and, a pair of retaining sheaths being formed about the opposite ends of the stent device and adjacent portions of the balloon, said retaining sheaths being tearable in response to the exertion of outward radial pressure by inflation of said balloon such that, when said balloon is inflated, said retaining sheaths will be torn and said stent device will be thereby released from engagement to said deployment catheter such that said stent may further self expand to its operative configuration without concurrent inflation of said balloon beyond that which is required to cause said balloon to exert outward pressure to tear said retaining sheaths.

2. The system of claim 1 wherein said retaining sheaths are each formed of perforated plastic which is shrunk about the ends of the stent device and portions of the balloon.

3. The system of device of claim 1 wherein said retaining sheaths are each formed of elastomeric material.

4. A method for delivering a self-expanding stent to a placement site within an anatomical passageway, said method comprising the step of:

a) providing a self-expanding stent which has a first operative configuration, and which is compactable to a second compact configuration;

b) providing a deployment catheter comprising an elongate catheter body having an inflatable balloon positioned thereon;

c) positioning said stent upon the balloon of said deployment catheter and causing said stent to be compacted to its compact configuration;

d) positioning a breakable stent holding member around at least a portion of said stent to hold said stent in its compact configuration upon said balloon;

e) advancing said deployment catheter, with said stent positioned thereon, into said anatomical passageway, such that the stent becomes located at its intended placement site;

f) inflating the balloon sufficiently to cause the stent holding apparatus to be broken, thereby releasing the stent and allowing the stent to self-expand to its operative configuration;

g) deflating said balloon;

h) removing said deployment catheter from said anatomical passageway such that the stent remains operatively positioned within said anatomical passageway.

5. The method of claim 4 wherein step b) further comprises the step of wrapping the ends of the stent with the sheath material which will tear under pressure when the balloon is inflated, and step d) further comprises the step of causing the sheath material to tear as the balloon is inflated.

6. The method of claim 4 wherein step a) further comprises the step of selecting the size of the stent and the number of convolutions defined thereby such that the expansion of the self-expansion of the stent to its operative configuration causes the stent to radially engage the anatomical passageway in a manner wherein the straight segments of the stent are no more than 5° out of parallel with one another.

7. The method of claim 4 wherein said method is carried out during an open surgical procedure and step b) further comprises the step of passing the balloon having the stent positioned thereupon through an incision which provides access into the anatomical passageway.

8. The method of claim 4 wherein said method is carried out by percutaneous insertion and step b) further comprises the step of passing the balloon having the stent positioned thereupon percutaneously through a tubular introducer and subsequently transluminally advancing said balloon into said anatomical passageway.

9. The method of claim 4 wherein said anatomical passageway comprises a blood vessel.

10. The method of claim 9 wherein said treatment site is an area of atherosclerotic plaque occlusion.

11. The method of claim 9 wherein said treatment site is a compressed area of said blood vessel.

12. The method of claim 4 wherein said method is carried out subsequent to an angioplasty at the treatment site.

13. The method of claim 12 wherein said method is carried out subsequent to a balloon dilation angioplasty at the treatment site.

14. The method of claim 12 wherein said method is carried out subsequent to an atherectomy procedure at the treatment site.

15. The method of claim 12 wherein said method is carried out subsequent to an ultrasonic ablation procedure at the treatment site.

16. The method of claim 12 wherein said method is carried out subsequent to a laser ablative procedure at the treatment site.

17. The method of claim 4 wherein the stent provided in step a) is the stent of claim 1.

18. A stent delivery and placement system, said system comprising:

a) a stent delivery catheter comprising an elongate catheter body having a proximal end, a distal end, and a radially enlargeable stent expander apparatus formed on said catheter body at a first location thereon;

said stent expander apparatus being initially disposed in a non-expanded state having a first outer diameter and being radially expandable to fully expanded state having a second outer diameter;

b) a self-expanding stent device mounted upon said stent expander apparatus of said delivery catheter, said stent device comprising a generally tubular article having a hollow inner passageway extending longitudinally therethrough;

said stent device being alternately configurable in
i) a radially compressed configuration wherein the internal passageway of stent has a diameter which is substantially the same as the first diameter of said expander apparatus when in it's non-expanded state; and,
ii) a fully expanded configuration wherein the inner/passageway said stent has a fully expanded diameter which is larger than said second diameter of said expander apparatus when in it's fully expanded state;

said stent being resiliently biased to it's fully expanded configuration such that, when unrestrained, said stent will self-expand to it's fully expanded configuration;

c) at least one retaining apparatus attached to said catheter and in abutting contact with at least a portion of said stent to retain said stent in it's radially compressed configuration, said retaining apparatus being constructed such that it's abutting contact with said stent will be disrupted when said stent expander apparatus is expanded to its second diameter, thereby causing said stent to become unrestrained and allowing said stent to further self-expand to its fully expanded configuration, without further expansion of said stent expander apparatus beyond it's second outer diameter.

19. The system of claim 18 wherein said self-expanding stent comprises a plurality of substantially straight wire segments disposed in a zig-zag configuration about a central longitudinal axis so as to form said generally cylindrical stent configuration having said hollow inner passageway extending longitudinally therethrough.

20. The system of claim 19 wherein said plurality of wire segments comprise resilient wire material which is formed to resiliently self-expand from said radially compressed configuration to said fully expanded configuration.

21. The system of claim 18 wherein said stent has opposite ends, and wherein said retaining apparatus comprises a pair of retaining sheaths disposed about the opposite ends of the stent, said retaining sheaths being anchored to portions of the delivery catheter body adjacent said opposite ends of said stent.

22. The system of claim 21 wherein said retaining sheaths have tearable regions formed therein such that, when said stent expander apparatus is expanded to it's said second diameter, said retaining sheaths will tear, thereby releasing said stent and allowing said stent to self-expand to its fully expanded configuration while said retaining sheaths remain anchored to said delivery catheter body.

23. The system of claim 22 wherein said retaining sheaths are formed of plastic film, and wherein said tearable regions comprise perforations formed in said plastic film.

24. The system of claim 18 wherein said stent expander apparatus comprises a balloon, and wherein at least one balloon inflation lumen extends longitudinally through at least a portion of said catheter body to permit passage of inflation fluid into and out of said balloon.

25. The system of claim 24 wherein said stent delivery catheter has an outer surface, and wherein said balloon comprises a generally cylindrical balloon formed about the outer surface of said catheter body at said first location.

26. In a stent delivery and placement system of the type wherein a self-expanding stent is advanced, in a radially compressed configuration, into an anatomical passageway having a known diameter, and subsequently allowed to self-expand to a fully expanded configuration wherein the outer diameter of said stent is at least as large as the known diameter of said anatomical passageway such that said stent is thereby frictionally held in a fixed position within said anatomical passageway, the improvement comprising:

a stent delivering and releasing catheter upon which said stent is initially mounted, said catheter being usable to advance said stent to a desired location within said anatomical passageway and to thereafter release said stent so as to allow said stent to self-expand and frictionally engage said passageway, said stent delivery catheter comprising:

i) an elongate catheter body having a proximal end a distal end;

ii) a stent expander apparatus disposed on said elongate catheter body, said stent expander apparatus being initially disposed in a non-expanded state having a first outer diameter, and being subsequently radially expandable to a fully expanded state having a second outer diameter, said second outer diameter of said stent expander apparatus being larger than its said first outer diameter, but smaller than the known diameter of said anatomical passageway;

said stent being initially mounted, in it's radially compressed configuration, upon the stent expander apparatus of said delivery catheter while said stent expander apparatus is in said non-expanded state; and, iii) at least one retaining apparatus attached to said catheter body in abutting contact with said stent to hold said stent in it's radially compressed configuration, said retaining apparatus being constructed such that it will be disrupted when said stent expander apparatus is expanded from it's first diameter to it's second diameter, said disruption of the stent retaining apparatus thereby causing said stent to become unrestrained and allowing said stent to further self-expand to it's fully expanded configuration in frictional engagement with said anatomical passageway, without further expansion of said stent expander apparatus beyond its second outer diameter.

27. The device of claim 26 wherein said stent expander apparatus comprises a balloon formed on said elongate catheter body, and a balloon inflation lumen extending longitudinally through at least a portion of said catheter body to permit passage of a balloon inflation fluid into and out of said balloon.

28. The device of claim 35 wherein said elongate catheter body has an outer surface, and wherein said balloon comprises a cylindrical balloon formed at a first location about the outer surface of said catheter body.

29. The device of claim 26 wherein said at least one retaining apparatus comprises a retaining sheath attached to said catheter body and extending about a portion of said stent to hold said stent in said radially compressed configuration upon said non-expanded stent expander apparatus, said sheath being disruptable by the expansion of said stent expander apparatus to it's fully expanded state having said second outer diameter.

30. The device of claim 29 wherein said retainer sheath has a tearable region formed therein such that said sheath will tear when said stent expander apparatus is expanded to it's fully expanded state, thereby releasing said stent to permit said stent to further self-expand to it's fully expanded configuration.

* * * * *